US010024432B2

(12) United States Patent
Linck-Lescanne et al.

(10) Patent No.: US 10,024,432 B2
(45) Date of Patent: Jul. 17, 2018

(54) SPECIAL SEAL GEOMETRY FOR EXHAUST GAS SENSORS FOR PRODUCING HIGH LEAK TIGHTNESS WITH RESPECT TO THE MEASUREMENT CHAMBER

(71) Applicant: Robert Bosch GmbH, Stuttgart (DE)

(72) Inventors: Markus Linck-Lescanne, Wannweil (DE); Juergen Wilde, Fellbach (DE); Bastian Buchholz, Stuttgart (DE); Narendiran Doraisamy, Tamilnadu (IN)

(73) Assignee: ROBERT BOSCH GMBH, Stuttgart (DE)

( * ) Notice: Subject to any disclaimer, the term of this patent is extended or adjusted under 35 U.S.C. 154(b) by 74 days.

(21) Appl. No.: 14/775,471

(22) PCT Filed: Feb. 27, 2014

(86) PCT No.: PCT/EP2014/053864
§ 371 (c)(1),
(2) Date: Sep. 11, 2015

(87) PCT Pub. No.: WO2014/139802
PCT Pub. Date: Sep. 18, 2014

(65) Prior Publication Data
US 2016/0025222 A1 Jan. 28, 2016

(30) Foreign Application Priority Data

Mar. 12, 2013 (DE) .......................... 10 2013 204 231
Jun. 28, 2013 (DE) .......................... 10 2013 212 570
Nov. 7, 2013 (DE) .......................... 10 2013 222 594

(51) Int. Cl.
*G01N 27/407* (2006.01)
*G01N 15/10* (2006.01)
(Continued)

(52) U.S. Cl.
CPC .......... *F16J 15/062* (2013.01); *F01N 13/008* (2013.01); *G01M 15/104* (2013.01); *G01N 27/4078* (2013.01); *G01N 27/407* (2013.01)

(58) Field of Classification Search
CPC ............. G01N 27/407; G01N 27/4077; G01N 27/4078; G01N 27/4071; Y10T 29/49007;
(Continued)

(56) References Cited

U.S. PATENT DOCUMENTS 4,796,923 A * 1/1989 Liggins ................. F16L 15/004
285/148.19
5,546,787 A * 8/1996 Hafele ............... G01N 27/4062
204/426
(Continued)

FOREIGN PATENT DOCUMENTS

DE     36 415 48     6/1988
DE     38 184 48     12/1989
(Continued)

OTHER PUBLICATIONS

Konrad Reif (editor), "Sensoren im Kraftfahrzeug" [Sensors in motor vehicles], 2nd edition, 2012, pp. 160-165.

*Primary Examiner* — Randy Gibson
*Assistant Examiner* — Gedeon M Kidanu
(74) *Attorney, Agent, or Firm* — Norton Rose Fulbright US LLP; Gerard Messina

(57) ABSTRACT

A sensor system, for sensing at least one property of a measured gas in a measured-gas space, includes a probe for sensing the property of the measured gas. The probe has at least one sensor element and at least one housing surrounding the sensor element. The housing is configured so that the sensor element in the housing is capable of being impinged upon with the measured gas. The sensor system also includes a receiving element connectable to a wall of the measured-gas space. The probe is introducible along an
(Continued)

insertion axis into the receiving element and securable in the receiving element. The probe is capable of being sealed off from the measured-gas space by at least one seal. The seal encompasses at least one linear seal.

14 Claims, 6 Drawing Sheets

(51) Int. Cl.
  *F16J 15/06* (2006.01)
  *F01N 13/00* (2010.01)
  *G01M 15/10* (2006.01)
(58) Field of Classification Search
  CPC ...... E21B 17/042; F16B 33/02; F16L 15/004; F16L 15/06; G01L 19/0645
  USPC ........... 73/31.05, 23.31, 23.32; 204/427, 428
  See application file for complete search history.

(56) References Cited

U.S. PATENT DOCUMENTS

| | | | |
|---|---|---|---|
| 6,068,746 A * | 5/2000 | Kojima | G01N 27/407 204/421 |
| 6,206,377 B1 * | 3/2001 | Weyl | G01N 27/407 204/424 |
| 6,383,355 B1 * | 5/2002 | Miyata | G01N 27/4077 204/427 |
| 6,453,726 B1 | 9/2002 | Gutierrez et al. | |
| 7,178,382 B2 * | 2/2007 | Noda | G01N 27/4078 73/23.2 |
| 7,222,408 B2 | 5/2007 | Tsuji | |
| 7,497,109 B2 * | 3/2009 | Satou | G01N 27/4077 73/31.05 |
| 7,695,027 B2 * | 4/2010 | Williams | F16L 19/06 285/342 |
| 7,784,837 B2 * | 8/2010 | Williams | F16L 23/06 285/342 |
| 2001/0035045 A1 * | 11/2001 | Hibino | G01N 27/407 73/31.05 |
| 2004/0040843 A1 * | 3/2004 | Weyl | G01N 27/4078 204/424 |
| 2004/0245482 A1 | 12/2004 | Sato | |
| 2005/0126261 A1 * | 6/2005 | Matsuda | G01N 27/407 73/31.05 |
| 2005/0155408 A1 | 7/2005 | Weyl et al. | |
| 2005/0217730 A1 * | 10/2005 | Doutt | F16K 15/044 137/539.5 |
| 2006/0213254 A1 * | 9/2006 | Satou | G01N 27/4077 73/31.05 |
| 2007/0175267 A1 * | 8/2007 | Yamauchi | G01N 27/407 73/31.05 |
| 2008/0028862 A1 | 2/2008 | Sonderegger et al. | |
| 2008/0105030 A1 * | 5/2008 | Wilde | G01N 27/4077 73/23.31 |
| 2012/0255356 A1 * | 10/2012 | Kume | G01N 27/4078 73/431 |
| 2013/0312485 A1 * | 11/2013 | Yonezu | G01N 27/4078 73/23.2 |

FOREIGN PATENT DOCUMENTS

| | | |
|---|---|---|
| DE | 197 349 435 | 3/1999 |
| DE | 1002 29 58 | 11/2001 |
| DE | 10 229 031 | 3/2004 |
| DE | 10 346 205 | 9/2004 |
| DE | 60 2005 002 375 | 6/2008 |
| DE | 10 2012 205 618 | 10/2012 |
| EP | 1561921 A1 | 8/2005 |
| JP | S5115526 A | 2/1976 |
| JP | S5355095 A | 5/1978 |
| JP | H08114573 A | 5/1996 |
| JP | 2001 221 769 | 8/2001 |
| JP | 2004258040 A | 9/2004 |
| JP | 2007162730 A | 6/2007 |
| JP | 2011099876 A | 5/2011 |
| WO | 01/86273 A1 | 11/2001 |

* cited by examiner

SPECIAL SEAL GEOMETRY FOR EXHAUST GAS SENSORS FOR PRODUCING HIGH LEAK TIGHTNESS WITH RESPECT TO THE MEASUREMENT CHAMBER

FIELD OF THE INVENTION

The present invention relates to a special seal geometry for exhaust gas sensors for producing high leak tightness with respect to a measurement chamber.

BACKGROUND INFORMATION

A plurality of different sensor systems for sensing at least one property of a measured gas in a measured-gas space are believed to be understood. A "gas property" is to be understood in principle as any physical and/or chemical property of the measured gas, such that one or also several properties of the measured gas can be sensed. Qualitative and/or quantitative sensing of at least one property of a measured gas can be accomplished using such a sensor system, for example sensing of at least one gas component of the measured gas, in particular sensing of a gas component in an air/fuel mixture, and/or sensing of a particle concentration in the measured gas, in particular a particulate mass concentration. Alternatively or additionally, however, other properties of the measured gas can also be sensed.

A sensor system for sensing a gas property can be configured, for example as discussed in Konrad Reif (editor), "Sensoren im Kraftfahrzeug" [Sensors in motor vehicles], 2nd edition, 2012, pp. 160-165, as a lambda probe, an embodiment both as a two-point lambda probe and as a broadband lambda probe, in particular as a planar broadband lambda probe, being described. Using a lambda probe it is possible to identify a gas proportion of a gas mixture in a combustion chamber, for example the air/fuel ratio λ that indicates the ratio of air to fuel. With two-point lambda probes it is possible to identify the air/fuel ratio only within a narrow range, for stoichiometric mixtures ($\lambda=1$). With a broadband lambda probe, conversely, identification over a wide range of λ can occur. These above-described lambda probes encompass a sensor element, usually a ceramic solid electrolyte which may be made of zirconium dioxide and yttrium oxide, or also solid layers, which may be made of zirconium dioxide. The sensor element is surrounded by a protective tube for protection from damage.

In sensor systems, for example in a lambda probe or, for example, in a particle sensor that can have the same geometric configuration as a lambda probe, for measuring a property of a measured gas in a measured-gas space, seals between various components of the sensor systems are categorically necessary. U.S. Pat. No. 6,453,726, for example, discusses a gas sensor having a sensor element partly surrounded by a housing and by an upper protective shield. A U-shaped seal is disposed between the upper protective shield and the housing in order to protect the sensor element. U.S. Pat. No. 7,222,408 furthermore describes a gas sensor having a sensor element that is disposed in hermetically sealed fashion in a housing. Gas sealing of a measured-gas space and of a reference-gas space inside the gas sensor is enabled by a crimping of the housing.

According to the related art, it is understood that a probe for sensing at least one gas property is introduced into a measured-gas space through a receiving element in a wall of the measured-gas space. A seal is disposed between the probe and the measured-gas space in order to prevent emergence of the measured gas from the measured-gas space. The seal can be configured, for example, as in DE 60 2005 002 375 T2, which proposes to ensure leak tightness of a connection between a probe and an exhaust manifold using a circular ring having the cross section of an outward-opening U.

Patent document DE 10 2012 205 618 A1 furthermore proposes a sensor that has a tubular sleeve made of metal as well as a tubular attachment element. The sleeve has a flange that is present in front of the attachment element and projects outward beyond a radially internal surface of the attachment element. A corner of the flange comes into contact with an oblique surface of the attachment element.

Patent document DE 100 22 958 A1 furthermore discusses a gas sensor, having a metallic housing, that is fastened by way of a hollow bolt in a measurement opening having a measured gas. Provided on a side of the housing which faces toward the measurement opening is a conically shaped surface with which the gas sensor sits on a conically shaped counter-surface. The conically shaped surfaces are at the same angle with respect to a longitudinal axis of the housing. A planar seal of this kind as recited in the existing art, as discussed e.g. in DE 60 2005 002 375 T2 with a sealing ring between a probe and a measured-gas space and in DE 100 22 958 A1, is disadvantageous, however, since a planar seal has a large sealing area. This makes possible only a poor sealing effect.

A seal of this kind having an additional sealing ring as recited in the existing art is additionally disadvantageous because installation of a probe, for example in an exhaust gas duct of an internal combustion engine, using a sealing ring can be complex and difficult, and it is moreover possible to lose the sealing ring during installation. With a planar seal having no sealing ring, a high degree of parallelism and flatness must be ensured for the mutually abutting surfaces. High costs for production, and high sensitivity to damage, can result therefrom.

A sensor system that exhibits excellent leak tightness between a probe and a measured-gas space, and that enables economical production and robustness for the seal, would therefore be desirable.

SUMMARY OF THE INVENTION

A sensor system for sensing at least one property of a measured gas in a measured-gas space is accordingly proposed, said system at least largely eliminating the disadvantages of known sensor systems for sensing at least one property of a measured gas in a measured-gas space. The intention in particular is to achieve sealing of the measured-gas space.

As discussed previously, the at least one property of the measured gas can in principle be any physical and/or chemical property of a measured gas. The property of the measured gas can be selected, for example, from the group consisting of: a proportion of at least one gas component in the measured gas, in particular an oxygen proportion and/or an NOx proportion; a particle loading of the measured gas; a temperature of the measured gas; a pressure of the measured gas. The at least one property can be, for example, a particle mass per unit volume, indicated e.g. in $kg/m^3$, or a number of particles per unit volume, indicated e.g. as particles/$m^3$. Other properties can in principle also be alternatively or additionally sensed.

The measured gas can in principle be any gas or gas mixture, for example exhaust gas, air, an air/fuel mixture, or also a different gas. The invention is usable in particular in the sector of automotive engineering, so that the measured-gas space can be an exhaust gas duct of an internal combustion engine. The measured gas can therefore in particular be an air/fuel mixture.

The sensor system encompasses a probe for sensing the at least one property of the measured gas. A "probe" can be understood in principle as any apparatus or combination of apparatuses that are configured for qualitative or quantitative sensing of the at least one property. For example, the probe can be configured to generate at least one measured signal that correlates with the at least one property to be sensed. The probe can be selected in particular from the group consisting of a lambda probe and a particle sensor. A different configuration of the probe, for example as a temperature sensor and/or a pressure sensor and/or an NOx sensor for sensing at least one gas component in the measured gas, for example for sensing the proportion of oxygen and/or nitrogen oxides in the measured gas, is nevertheless also possible in principle.

The probe has at least one sensor element and at least one probe housing surrounding the sensor element. A "sensor element" can be understood in principle as any measurement element or combination of measurement elements, for example a sensor chip, that are configured for qualitative or quantitative sensing of the at least one property. The sensor element can encompass, for example, a sensor chip and/or an electronic measurement circuit. The sensor element can be configured in particular to generate at least one measured signal that correlates with the at least one property to be sensed. The sensor element can be, in particular, a ceramic sensor element. The sensor element can be, in particular, a ceramic sensor element that has at least one ceramic body and at least two electrodes connected to the ceramic body. The ceramic body can have at least one ceramic solid electrolyte.

The measurement principle of the sensor element can be based in particular on the electrolytic property of certain solids. Ceramic solid electrolytes, for example zirconium dioxide ($ZrO_2$), in particular yttrium-stabilized (YSZ) or scandium-doped zirconium dioxide (ScSZ), are particularly suitable as solids. Alternatively or additionally, the sensor element can have, for example, at least two electrodes, for example on a measurement surface, in particular a ceramic measurement surface, and can be configured, for example, to sense an electrical resistance between the at least two electrodes, which resistance can be influenced, for example, by a particle loading of the measured gas. A sensor element of this kind can furthermore, as a rule, encompass a heating element in order to ensure a suitable functioning temperature. Other configurations are, however, also conceivable in principle.

A "probe housing" can be understood in the context of the present invention in principle as a component that completely or partly surrounds the probe, for example a casing that surrounds the probe, in particular the sensor element, and protects it from thermal and mechanical influences. The probe housing can in particular encompass at least one interior space in which the at least one sensor element is disposed. The probe housing can in particular be manufactured entirely or partly from a mechanically rigid material that completely or partly protects the probe with respect to mechanical influences, for example from a metallic material.

The probe housing is configured in such a way that the sensor element in the probe housing can be impinged upon by the measured gas. For example, the probe housing can have an opening through which the measured gas can penetrate into the probe. For example, the probe housing can encompass at least one protective tube. A "protective tube" is to be understood as a tube, made e.g. of metal, that protects the sensor element from thermal and mechanical influences. The protective tube can have at least one interior space and at least the sensor element received in the interior space. The protective tube can be in particular a double-walled protective tube that has an annular gap. For example, the measured gas can flow through the annular gap into the interior space. In particular, the protective tube can point into the measured-gas space in tilted fashion with respect to an insertion axis, in particular with respect to an insertion axis described in further detail below. The term "tilted" can be understood to mean that the protective tube can be disposed at an angle with respect to the insertion axis. The protective tube can have, for example, at least one inlet opening and at least one outlet opening, for example at least one inlet opening that is in communication with the annular gap and at least one outlet opening that is in communication with the interior space. For example, the probe housing can be configured in such a way that the outlet opening is disposed lower down in the measured-gas space, for example in a flow tube, than the inlet opening. It is thereby possible to ensure, for example by way of pressure differences, a flow of measured gas from the inlet opening through the interior space to the outlet opening. Other embodiments are, however, also possible in principle.

The sensor system furthermore has a receiving element connectable to a wall of the measured-gas space. A "receiving element" is to be understood as a component that is configured to introduce the probe into the measured-gas space. This wall can be, for example, a tube wall of a flow tube or another type of measured-gas space. The receiving element can be, for example, permanently connected to the wall, or can also be reversibly connectable to the wall. The receiving element can completely surround the probe. The receiving element may annularly surround the probe.

The probe is introducible into the receiving element along an insertion axis, and securable in the receiving element. The insertion axis can be defined here by the insertion direction of the probe into the receiving element. For example, the insertion axis can extend substantially perpendicularly to a tube axis of a flow tube, for example with a deviation from the perpendicular of no more than 20°, in particular no more than 10°. The probe can in particular be detachably connectable to the receiving element.

The receiving element can be configured in particular as a weld-in fitting. For example, the weld-in fitting can be inserted into a bore in the measured-gas space and then welded and/or otherwise connected, which may be by material attachment. The receiving element can furthermore be manufactured from steel, in particular corrosion-resistant steel. For example, the probe may be secured in the receiving element nonpositively, in particular by way of a screw connection, in particular by way of a detachable screw connection, and/or positively, for example by press-fitting, in particular by detachable press-fitting.

The sensor system can furthermore have at least one securing element that is configured to secure the probe nonpositively in the receiving element. For example, the securing element can be configured to press the probe against the receiving element and/or vice versa. The housing and/or the receiving element can remain rigid and undeformed during a securing operation, for example during screw connection, or can also deform entirely or partly, for example elastically or plastically, during the securing operation.

A "securing element" is to be understood as a component with which the probe can be fastened in the receiving element. The securing element can in particular have at least one thread. The thread can have in particular a housing-side thread and a receiving element-side thread. The housing-side thread can encompass a coupling screw. The securing element can be implemented, for example with at least one coupling screw and/or at least one coupling nut. The threads can be screw-connected to one another for nonpositive securing. Other configurations are, however, also possible in principle. For example, the securing element can be constituted entirely or partly from a metallic material, for example at least one steel, which may be a stainless steel. The securing element, in particular the coupling screw and/or coupling nut, can thus be manufactured in particular from a material selected from the group consisting of a material (in particular a stainless steel) having the material number 1.4104; a material (in particular a stainless steel) having the material number 1.4105; a material (in particular a stainless steel) having the material number 1.4301; a material (in particular a stainless steel) having the material number 1.4303; a material (in particular a stainless steel) having the material number 1.4305; and a material (in particular a stainless steel) having the material number 1.4016.

With the probe introduced into the receiving element, the receiving element can surround the housing of the probe in such a way that the housing projects partly into the measured-gas space and is partly disposed outside the measured-gas space. "Projects partly into the measured-gas space" is to be understood to mean that a lower part of the housing, in particular the double-walled protective tube, can be disposed in the measured-gas space, while an upper part of the housing is disposed outside the measured-gas space. In particular, the housing can project through the receiving element into the measured-gas space.

The probe can be sealed off from the measured-gas space by at least one seal. A "seal" is to be understood as an apparatus that is configured to prevent a material transfer, in particular an emergence of measured gas from the measured-gas space. The seal can be configured in particular to be media-tight, for example tight with respect to the measured gas and/or with respect to other fluid media. The seal can be configured in particular to be pressure-tight, for example up to a pressure of 2 bar or more, for example a pressure of up to 10 bar, 100 bar, 1 kbar, or more.

"Sealing off" the probe with respect to the measured-gas space can thus be understood generally to mean an embodiment of the seal by which an emergence of substances from the measured-gas space, in particular an emergence of measured gas, through an interstice between the housing and the receiving element and/or between the housing and the wall of the measured-gas space, is prevented. The term "sealable" encompasses not only the possibility of sealing but also the instance in which the probe is sealed off from the measured-gas space.

With the probe introduced into the receiving element, the seal can in particular be disposed between the measured-gas space and the securing element. In particular, the seal can be constituted between the receiving element and the housing. In particular, the seal can be constituted directly between the receiving element and the housing, so that a gap between the receiving element and the housing is directly sealed by the seal.

The at least one seal has at least one linear seal. A "linear seal" can be understood to mean that the surfaces forming the seal make contact linearly. The linear shape may have an unmeasurably small line width. Upon securing of the probe, the probe can be pressed against the receiving element and the probe can be secured nonpositively in the receiving element. Elastic and plastic deformations can occur as a result of an application force acting in this context, and the width of the line can change. Upon action of the application force, the line widths of the linear seal can be, for example, in the range of <1 mm, in particular <500 micrometers. Other line widths are, however, also possible, since, as will be discussed below in further detail, the line widths can be dependent on a plurality of boundary conditions.

For example, the housing can be supported on the receiving element or vice versa, and the sealing element, which is configured as a linear seal, can be constituted in the region in which the housing is supported on the receiving element or in which the receiving element is supported on the housing.

The probe can be sealed off from the measured-gas space by one or also by several seals. If several seals are provided, then at least one of those seals is configured as a linear seal. In addition, one or several further seals can be provided which can be configured as linear seals or also as nonlinear seals. If several seals are provided, it may be if at least that seal which is immediately adjacent to the measured-gas space is configured as a linear seal. This can be done, for example, in such a way that on the way from the measured-gas space into an external space, the measured gas must first pass the linear seal in order then, optionally, to traverse one or several further seals.

The seal can, in particular, have at least two linear seals. In particular, the sensor system can be configured in such a way that the housing is flexibly clampable between two linear seals and/or that the two linear seals are configured in such a way that the housing is flexible clampable in terms of a tilting motion around an axis of the sensor system.

The seal, in particular the linear seal, can in particular be formed by the receiving element and the housing, so that the receiving element and the housing may themselves form the linear seal.

As will be discussed in further detail below, in particular by way of at least one securing element the housing can be pressed against the receiving element, and/or the receiving element can be pressed against the housing. The securing element can encompass in particular at least one nut and/or at least one screw, for example at least one coupling nut and/or at least one coupling screw.

As set forth above, the line width of the linear seal can depend greatly on the boundary conditions for securing the probe in the receiving element. The line width can depend in particular on a tightening torque of a securing screw and/or on a geometry of the sealing surfaces. Without an application force the line width may be, within production tolerances, insignificantly thin, for example <1 mm or <500 micrometers. With an application force, on the other hand, elastic and/or plastic deformations can occur which can then modify the geometry of the sealing surface. This modification can then at first reduce a maximally achievable sealing pressure due to an enlargement of the sealing area. On the other hand, however, elastic and/or plastic deformations can also help to compensate for small production variations and irregularities.

The utilization of linear seals is believed to be understood in principle from other sectors of the related art. A linear seal is believed to be understood, for example, from DE 10 234 615 in the context of a crimp-joined subassembly of tubes having a metal-to-metal linear seal, and from U.S. Pat. No. 7,373,827 in the context of a high-pressure sensor. Patent document DE 34 41 918 discusses a linear seal having a conical radius in the context of a plate-shaped filter insert for vehicle cabin air filters. A conical-to-conical sealing geometry is furthermore described, for example, in DE 234 90 89 in the context of a stuffing box-free solenoid valve for nuclear engineering facilities, in DE 4 242 290 in the context of high-pressure fluid filtration systems, in U.S. Pat. No. 4,169,967 for insulation of electrical leads, and in DE 29 01 507 in the context of a valve having a polymeric material. Patent document DE 36 41 548, for example, discloses a knife edge seal, for example in closures of containers and tubes. In the context of the embodiment of the proposed linear seal, reference may be made to the embodiment of the linear seals as recited in the existing art, with the additional features according to the present invention. A different embodiment of the linear sealing element is, however, also possible in principle.

The housing can in particular have at least one supported element. A "supported element" is to be understood as a component that is configured to be supported on another component. The supported element can surround the probe, for example annularly, in particular in the form of an annular shoulder.

The supported element can be configured, in particular, entirely or partly as a spring element. A "spring element" is to be understood generally as an element that exhibits at least partly elastic properties. In particular, the supported element can be configured at least partly as a cup spring. In particular, the supported element can be configured at least partly as an annular shoulder, the annular shoulder forming the spring element, in particular the cup spring.

The housing and/or the supported element can be constituted, for example, entirely or partly from a metallic material, for example at least one steel, which may be a stainless steel. The housing and/or the supported element can in particular, each mutually independently and each entirely or partly, be manufactured from a material selected from the group consisting of a material (in particular a stainless steel) having the material number 1.4104; a material (in particular a stainless steel) having the material number 1.4105; a material (in particular a stainless steel) having the material number 1.4301; a material (in particular a stainless steel) having the material number 1.4303; a material (in particular a stainless steel) having the material number 1.4305; and a material (in particular a stainless steel) having the material number 1.4016.

The supported element can in particular have at least one element, in particular one surface element, selected from the group consisting of a conical surface, and a surface that has a radius. A "conical surface" is to be understood as a surface that is beveled at an angle, in particular a chamfer. A "surface that has a radius" can be understood as an arbitrarily rounded surface. The supported element can in principle be a separate component that can be mounted onto the probe, after the process of manufacturing the probe, by way of a joining process, for example by welding or soldering or also other processes. Alternatively, the supported element can already be fitted on during the process of manufacturing the probe, for example in a deep drawing process. The conical surface, in particular the chamfer, and the surface that has a radius, can be produced on the supported element, for example, by milling or planing.

The receiving element can furthermore have at least one sealing element. A "sealing element" is to be understood in principle as a component of the receiving element on which the supported element of the probe can be supported. The sealing element can have an element, in particular a surface element, selected from the group consisting of a conical surface, a surface that has a radius, in particular a rounded surface. A "conical surface" of the sealing element is to be understood as a surface that is beveled at an angle. The sealing element can in principle be a separate component that can be mounted onto the receiving element, after the process of manufacturing the receiving element, by way of a joining process, for example by welding or soldering or also other processes. Alternatively, the sealing element can already be fitted on during the process of manufacturing the receiving element, for example in a deep drawing process. The conical surface and the surface that has a radius can be produced on the receiving element, for example, by milling or planing.

The supported element and the sealing element can form the seal or constituents thereof, in particular the linear seal. The linear seal can in particular be a seal in which the seal-forming components, for example the supported element and the sealing element, make contact linearly. With the probe introduced into the receiving element, the supported element can be supported on the sealing element. The linear seal can be configured to prevent a material transfer, in particular an emergence of the measured gas from the measured-gas space. The linear seal can be selected from the group consisting of a conical-to-conical seal, a conical-to-radius-shaped seal.

In a conical-to-conical seal, for example, the supported element and the sealing element can each have a conical surface. In a conical-to-radius-shaped seal, for example, one element selected from the supported element and the sealing element can have a conical surface and the other element can have a radius, for example an arbitrarily rounded surface.

In an exemplary embodiment the supported element and the sealing element can have a conical-to-conical seal, the supported element and the sealing element each having conical surfaces with a different taper angle. A "taper angle" is to be understood as the angle, in particular with respect to a horizontal axis, at which the conical surface can be generated, in particular can be beveled. With the probe introduced into the receiving element, the conical surface of the supported element can be inclined with respect to the conical surface of the sealing element. The conical surface of the receiving element can be inclined 10°, particularly 20°, with respect to the conical surface of the sealing element. For example, the conical surface of the supported element can have been manufactured with a different taper angle than the conical surface of the sealing element. In particular, the conical surface of the supported element can be beveled at a different angle than the conical surface of the sealing element. The taper angle of the conical surface of the supported element can be smaller than the taper angle of the conical surface of the sealing element. The mutual inclination angle of the conical surfaces can in principle vary and, for example, can be adapted to customer requirements.

For example, the inclination angle can be a shallow angle, for example an angle<45°, in particular an angle<30° or an angle of 20° or less. In principle, however, the inclination angle can be varied arbitrarily. Large angles, however, for example angles>60°, in many cases result in a technical challenge in that mutual positioning of the elements becomes difficult. A result of steep flanks, for example, can be that self-centering is made difficult, and a location and/or position of the linear seal can also be defined less unambiguously. The aforesaid challenges can exist especially in a context of production variations in the conical surfaces. The aforementioned shallow angles of less than 45° may therefore be used in principle, for example angles of 20°. The sealing effect that is to be achieved can in principle be varied and adapted by adjusting the inclination angles and the geometric design of the components.

In particular, with the probe introduced into the receiving element, the supported element can be supported linearly on the beveled surface of the sealing element and the sealing element can thus form a linear seal. "Linear" support can be understood to mean that the surfaces of the supported element and of the sealing element make contact linearly.

In a further exemplary embodiment, the supported element and the sealing element can have a conical-to-radius-shaped seal. One element selected from the supported element and the sealing element can have a conical surface, and the other element a radius. In particular, the supported element of the probe can have a radius-shaped surface and, with the probe introduced into the receiving element, can be supported linearly on the beveled surface of the sealing element and thus form a linear seal.

The supported element and the sealing element can be configured in self-centering fashion. A self-centering embodiment can be achieved by the conical shape of one and/or both elements selected from the group consisting of the supported element and the sealing element, in combination with the linear support of the supported element on the sealing element.

In a further embodiment the seal can have at least two linear seals. The supported element can be embedded in an axial direction between the linear seals. For example, the supported element can be secured between the linear seals at an angle to an axis of the sensor system, for example to the insertion axis, in particular at a tilt angle with respect to the axis.

The linear seals can encompass a first linear seal and a second linear seal. The first linear seal can be formed by the receiving element and the housing, in particular the supported element. With regard to an embodiment of the first linear seal, reference may be made to the above-described linear seal between the receiving element and the housing.

The second linear seal can be formed by the housing, in particular the supported element, and a securing element for securing the housing in the receiving element, in particular a coupling screw and/or a coupling nut. In particular, with the probe introduced into the receiving element, the supported element and the securing element can make contact linearly. The second linear seal can in particular be respectively selected from the group consisting of a conical-to-conical seal, a conical-to-radius-shaped seal.

In the context of a conical-to-conical seal of the supported element and the securing element, for example, the supported element and the securing element, in particular a coupling screw and/or a coupling nut, can each have a conical surface. The conical surfaces of the supported element and of the securing element can be, in particular, conical surfaces having different taper angles. The mutual inclination angle of the conical surfaces can in principle vary and, for example, can be adapted to customer requirements In the context of a conical-to-radius-shaped seal, for example, one element selected from the supported element and the securing element can have a conical surface, and the other element a radius, for example an arbitrarily rounded surface. For example, the supported element of the probe can have a radius-shaped surface and, with the probe introduced into the receiving element, can make contact linearly with a conical surface of the securing element and form a linear seal. For example, the securing element can have a radius-shaped surface and, with the probe introduced into the receiving element, can make contact linearly with a conical surface of the supported element and form a linear seal.

Regarding the configuration of the conical-to-conical seal and the conical-to-radius-shaped seal, reference may be made to the description of the conical-to-conical seal and the conical-to-radius-shaped seal of the supported element and sealing element.

The supported element and the securing element can be configured in self-centering fashion. A self-centering embodiment can be achieved by the conical shape of one and/or both elements selected from the group consisting of the supported element and the securing element, in combination with the linear contact between the supported element and the securing element.

The embodiments, in particular, can be as follows:
i) The first linear seal can be configured as a conical-to-conical seal and the second linear seal as a conical-to-conical seal;
ii) the first linear seal can be configured as a conical-to-conical seal and the second linear seal as a conical-to-radius-shaped seal;
iii) the first linear seal can be configured as a conical-to-radius-shaped seal and the second linear seal as a conical-to-conical seal;
iv) the first linear seal can be configured as a conical-to-radius-shaped seal and the second linear seal as a conical-to-radius-shaped seal.
Other embodiments may also be provided.

The sensor system according to the present invention allows a seal to be achieved between the probe and the exhaust gas duct of an internal combustion engine. Thanks to the sealing principle of the linear seal, a high sealing pressure is achieved because of the small sealing area, the sealing pressure being defined as force per unit area. The high sealing pressure results in greater robustness with regard to loosening of the connection between the receiving element and probe with respect to temperature fluctuations and vibratory oscillations, in particular vibrations, as compared with seals that are configured according to the existing art. A further advantage as compared with seals that are configured as recited in the existing art with a flat seal, in particular with a sealing ring, is that one less component is required. The difficult and complex installation of that component can thereby be avoided, and costs can be reduced.

The flexible clamping of the housing between two linear seals allows an improvement in the measurement sensitivity and diagnostic capability of the probe as compared with the existing art, and enables a high tolerance with respect to production variations. In addition, excellent leak tightness can be achieved with an embodiment of the seal with two linear seals. An embodiment of the supported element as a cup spring is also advantageous, since the probe's vibration resistance is improved.

Further details and features are evident from the description below of exemplary embodiments that are schematically depicted in the Figures.

DETAILED DESCRIPTION

Figure 1:
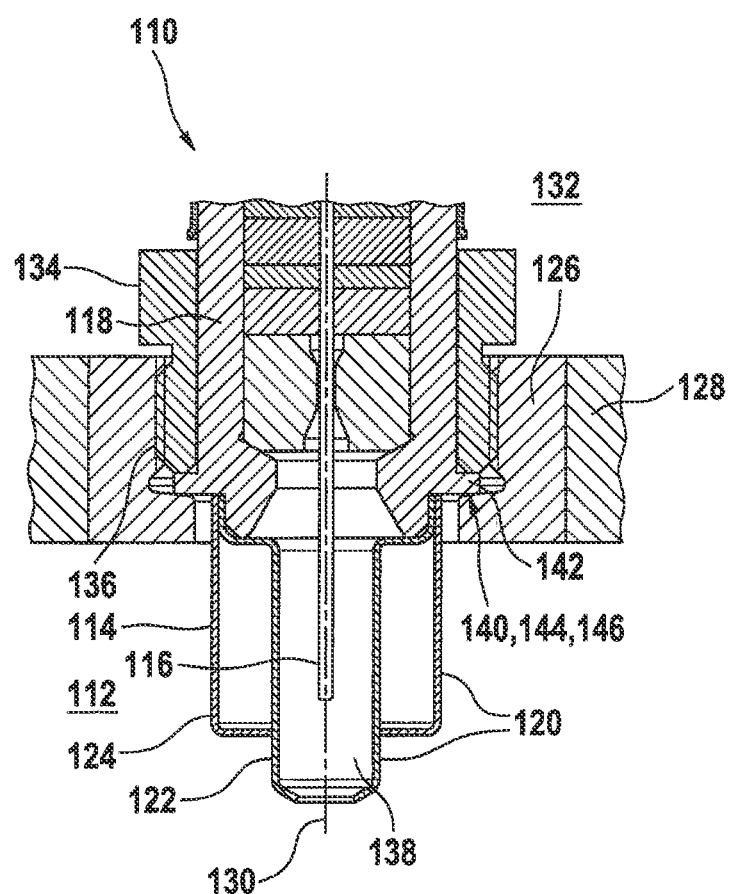
FIG. 1 shows an exemplifying embodiment of a sensor system according to the present invention.

An exemplifying embodiment of a sensor system 110 according to the present invention for sensing at least one gas property of a measured gas in a measured-gas space 112 is depicted schematically in FIG. 1. Sensor system 110 has a probe 114 for sensing the property of the measured gas in measured-gas space 112. Probe 114 can be configured in particular as a lambda probe, which is used in particular to sense a gas component in an air/fuel mixture in an exhaust gas duct of a motor vehicle. Measured-gas space 112 can accordingly be, in particular, a flow tube. Probe 114 can encompass a sensor element 116, configured for example as described in Konrad Reif (editor), "Sensoren im Kraftfahrzeug" [Sensors in motor vehicles], 2nd edition, 2012, pp. 160-165. Other embodiments of sensor element 116 are, however, possible in principle; for example, sensor element 116 can also be configured as a temperature sensor element or pressure sensor element or particle sensor element. Probe 114 can have a housing 118 having a protective tube 120 that surrounds sensor element 116 in order to protect it from thermal as well as mechanical influences. Protective tube 120 can be configured as a double-walled protective tube that encompasses an inner protective tube 122 and an outer protective tube 124.

Sensor system 110 has a receiving element 126 that can be connected to a wall 128 of measured-gas space 112. The connection can be permanent, for example by way of a welded connection. The connection can be configured as a reversible connection, for example by way of a screw connection, in which probe 114 is detachably connected to receiving element 126. Receiving element 126 can be configured, for example, as a weld-in fitting, for example made of corrosion-resistant steel. The weld-in fitting can be welded to wall 128 of measured-gas space 112. Probe 114 is introducible from an external region 132 through receiving element 126 into measured-gas space 112 along an insertion axis 130. With probe 114 introduced, receiving element 126 can completely surround probe 114. In particular, probe 114 can be annularly surrounded by receiving element 126. Housing 118 of probe 114 can, in the state introduced into receiving element 126, partly project into measured-gas space 112 and partly be disposed outside measured-gas space 112. In particular, housing 118 can project through receiving element 126 into measured-gas space 112. For example, a part, for example 50%, of double-walled protective tube 120, which may be 80%, particularly 90% of double-walled tube 120, can project into measured-gas space 112.

Sensor system 110 can furthermore have at least one securing element 134 in order to secure probe 114 on receiving element 126. Probe 114 can be pressed against receiving element 126, and nonpositively secured, by securing element 134. Securing element 134 can have at least one thread 136 that can encompass a housing-side thread and a receiving element-side thread. The housing-side thread can encompass a coupling screw. For example, probe 114 can be secured nonpositively, by screw connection, using a coupling nut and/or at least one coupling nut. FIG. 1 depicts an exemplifying embodiment in which probe 114 can be fastened in a weld-in fitting with a coupling screw.

Double-walled protective tube 120 can furthermore have an interior space 138. Sensor element 116 can be received in interior space 138. With probe 114 introduced into receiving element 126, measured gas can penetrate into interior space 138. Double-walled protective tube 120 can have for that purpose an annular gap so that the measured gas can flow through the annular gap into interior space 138.

Probe 114 can be sealed off from measured-gas space 112 by a seal 140. Seal 140 is configured as a linear seal. With probe 114 introduced into receiving element 126, seal 140, in particular a first linear seal 146, can be disposed between measured-gas space 112 and securing element 134 and can prevent emergence of measured gas from measured-gas space 112. Housing 118 can encompass a supported element 142. Supported element 142 can be of annular configuration and can surround probe 114 in the form of an annular shoulder. Receiving element 126 can furthermore have a sealing element 144. Linear seal 140, in particular first linear seal 146, can be formed by sealing element 144 and supported element 142. With probe 114 introduced into receiving element 126, supported element 142 can be supported on sealing element 144, a surface of supported element 142 and a surface of sealing element 144 in particular being in contact. The surfaces are in contact, in particular, linearly. The geometric embodiment of the mutually contacting surfaces of supported element 142 and of sealing element 144 can be conical-to-conical (both surfaces are configured conically, in particular as a beveled surface) or conical-to-radius-shaped (the surface of sealing element 144 is, for example, configured conically and the surface of supported element 142 is configured as a rounded surface that has a radius. A conical-to-radius-shaped seal 140, in particular first linear seal 146, can also be achieved by a conical embodiment of the surface of supported element 142 and of a surface of sealing element 144 which is of rounded configuration.

Figure 2A:
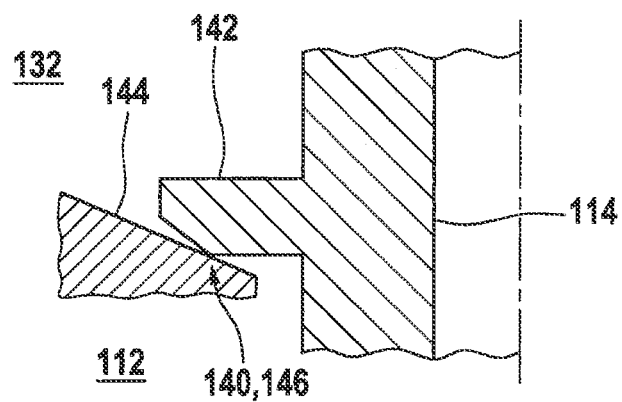
FIGS. 2A and 2B show exemplifying embodiments of a linear seal according to the present invention.

An exemplary embodiment of linear seal 140 according to the present invention, in particular of first linear seal 146, is shown in FIG. 2A. In this embodiment linear seal 140, in particular first linear seal 146, is configured as a conical-to-conical seal. Sealing element 144 and supported element 142 can each have a conical surface. The conical surface of sealing element 144 can have been generated with a different angle, in particular a different taper angle, than the conical surface of supported element 142. For example, the angle with which the conical surface of sealing element 144 was generated can be greater than the angle of the conical surface of supported element 142. In particular, the conical surface of sealing element 144 can be inclined 10°, which may be 15°, and particularly 20° with respect to the conical surface of supported element 142. This mutual inclination angle of the conical surfaces can in principle vary and, for example, can be adapted to customer requirements. The conical surfaces of sealing element 144 and of supported element 142 contact one another in such a way that upon superimposition they form a linear seal 140, in particular first linear seal 146. The conical shape of sealing element 144, together with a linear superimposition of the conical surfaces, can result in self-centering of the probe in receiving element 126.

Figure 2B:
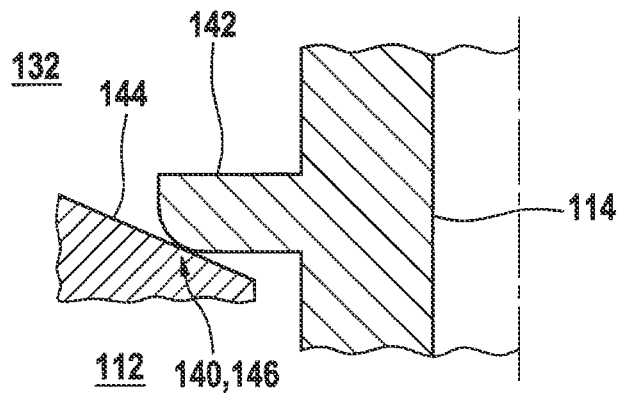

FIG. 2B depicts a further embodiment of linear seal 140 according to the present invention, in particular of first linear seal 146. Sealing element 144 can have a conical surface and supported element 142 a radius, in particular a rounded surface. An embodiment in which sealing element 144 has a radius and supported element 142 a conical surface is also possible in principle. The conical surface of sealing element 144 and the rounded surface of supported element 142 contact one another in such a way that upon superimposition they form a linear seal 140, in particular first linear seal 146, which is configured to seal off probe 114 from measured-gas space 112.

Figure 3A:
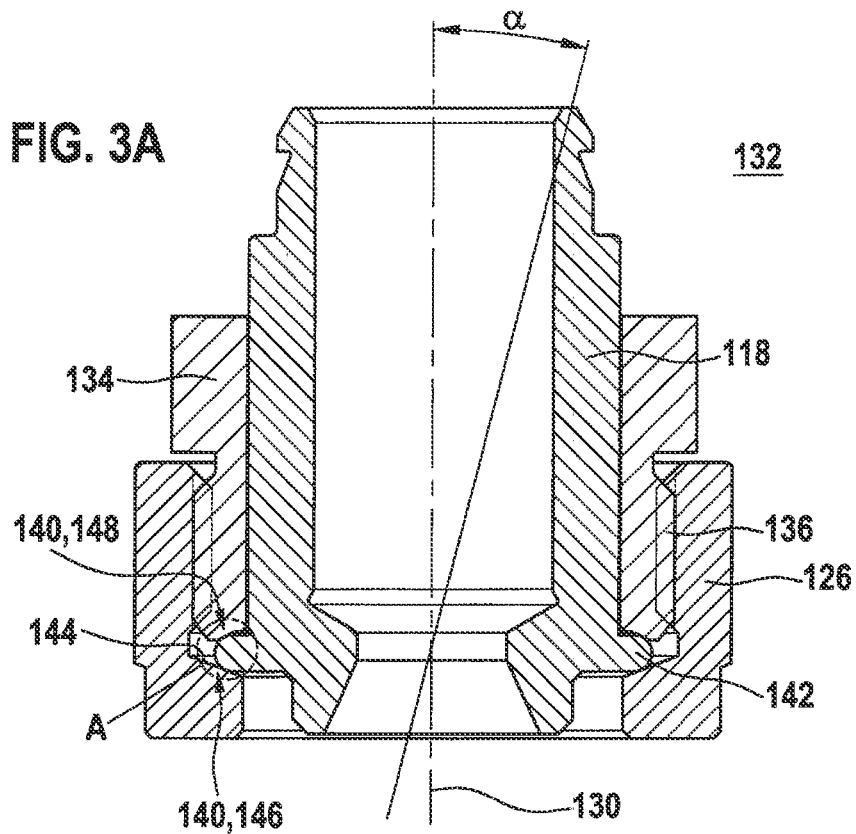
FIGS. 3A and 3B show a further exemplifying embodiment of the seal according to the present invention.
Figure 3B:
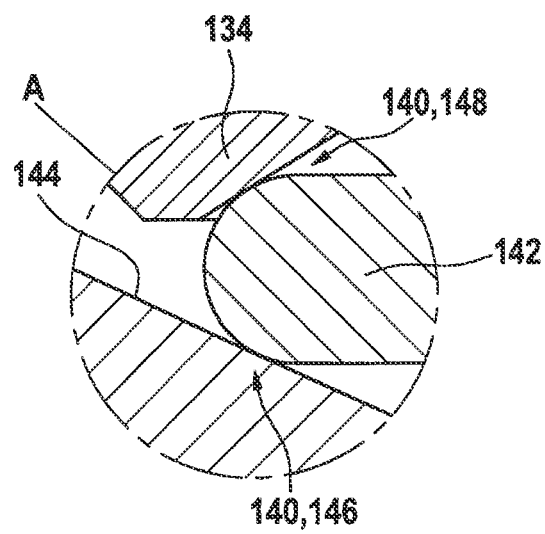

FIG. 3A shows a further exemplifying embodiment of linear seal 140 according to the present invention. An enlargement of portion A of the Figure is depicted in FIG. 3B. In this exemplifying embodiment, seal 140 can encompass first linear seal 146 and a second linear seal 148. First linear seal 146 can be formed by receiving element 126 and by housing 118, in particular by supported element 142. Sealing element 144 can have a conical surface and supported element 142 a radius, in particular a rounded surface. The conical surface of sealing element 144 and the rounded surface of supported element 142 contact one another in such a way that upon superimposition, they form first linear seal 146. Second linear seal 148 can be formed by housing 118, in particular supported element 142, and by a securing element 134 for securing housing 118 in the receiving element. Securing element 134 can be configured in particular as a coupling screw and/or a coupling nut. Securing element 134 can have a conical surface and supported element 142 a radius, in particular a rounded surface. The conical surface of securing element 134 and the rounded surface of supported element 142 make contact with one another in such a way that upon superimposition, they form second linear seal 148.

Supported element 142 can be embedded in an axial direction between the linear seals. Housing 118 can be clamped flexibly between first linear seal 146 and second linear seal 148, and/or first linear seal 146 and second linear seal 148 can flexibly clamp housing 118 in terms of a tilting motion around an axis of sensor system 110, in particular a tilting motion at an angle α with respect to insertion axis 130. Supported element 142, in particular probe 114, can thus be axially aligned between first linear seal 146 and second linear seal 148.

Figure 4A:
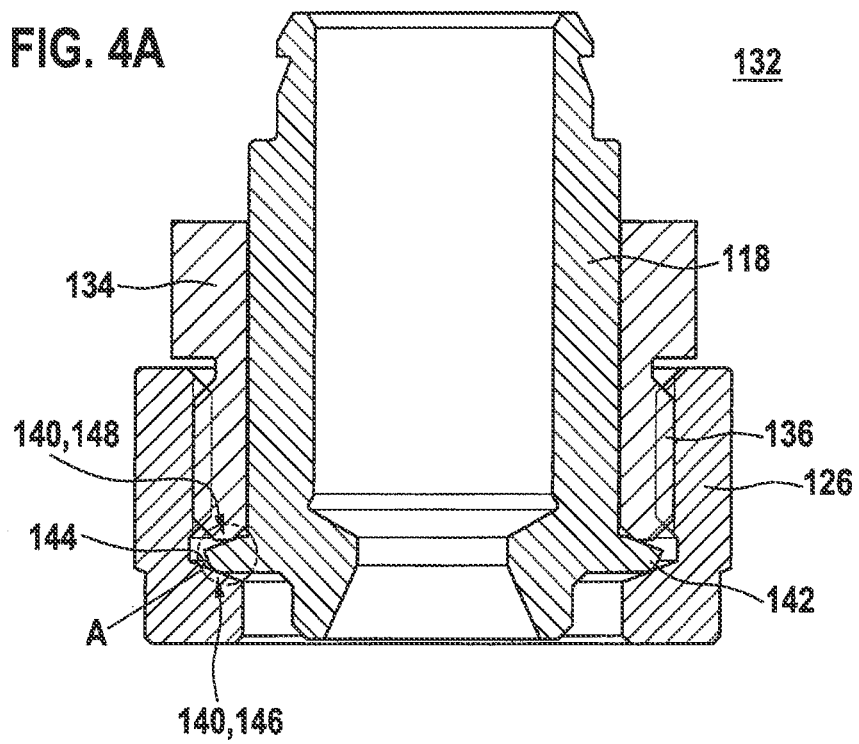
FIGS. 4A and 4B show a further exemplifying embodiment of the seal according to the present invention.
Figure 4B:
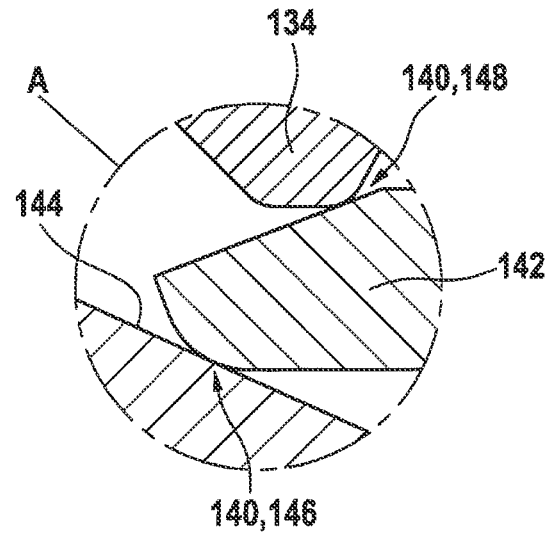

FIG. 4A shows a further exemplifying embodiment of seal 140 in which seal 140 can encompass first linear seal 146 and second linear seal 148. An enlargement of portion A of the Figure is depicted in FIG. 4B. First linear seal 146 can be formed by a conical surface of sealing element 144 and a rounded surface, in particular a radius, of supported element 142. Second linear seal 148 can be constituted by a rounded surface, in particular a radius, of securing element 134 and a conical surface of supported element 142.

Figure 5A:
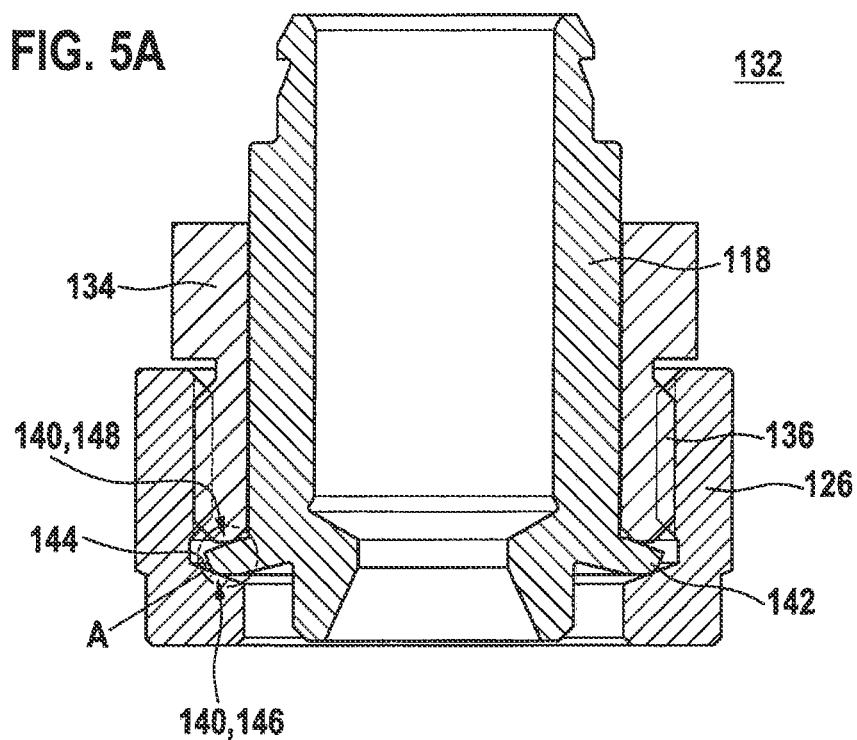
FIGS. 5A and 5B show an exemplifying embodiment of the seal according to the present invention having a supported element according to the present invention.
Figure 5B:
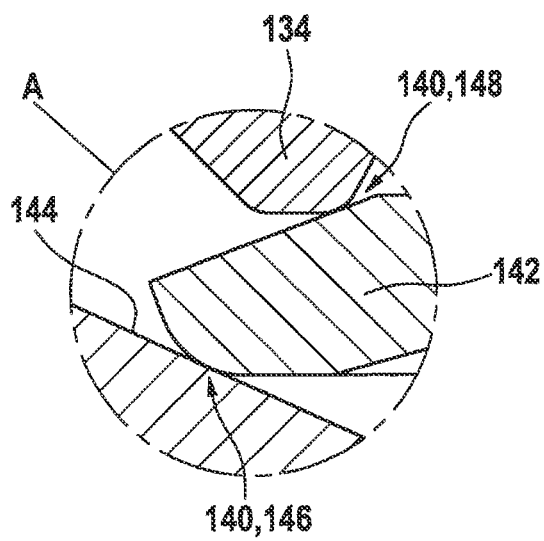
Figure 6A:
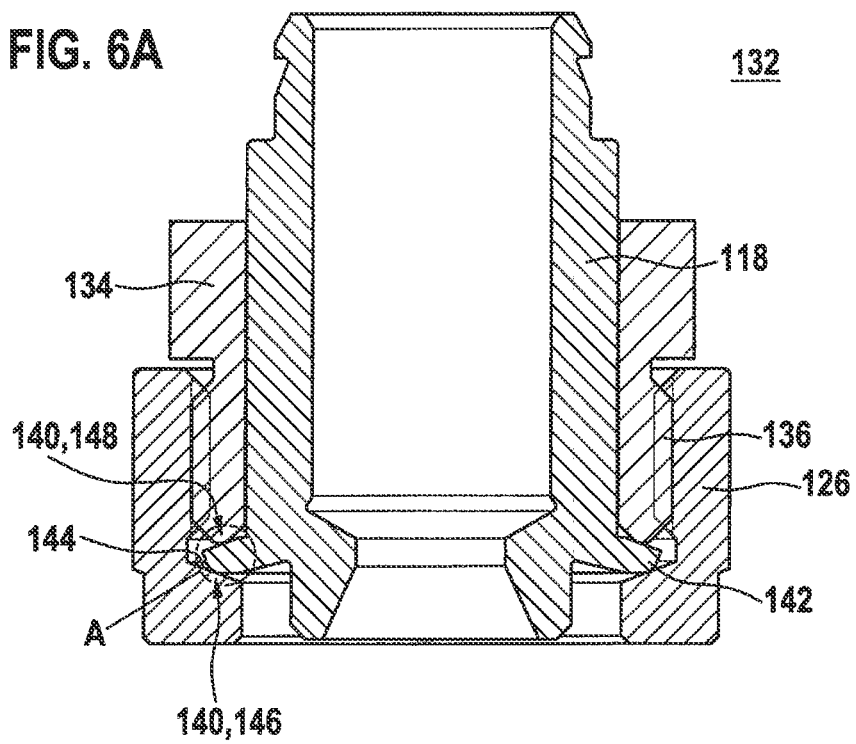
FIGS. 6A and 6B show an exemplifying embodiment of the seal according to the present invention having the supported element according to the present invention.
Figure 6B:
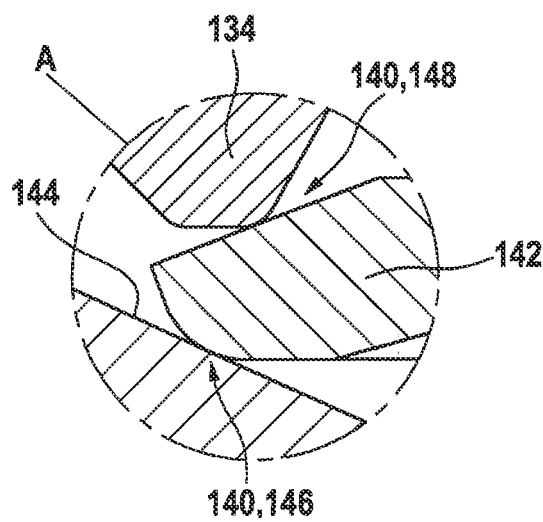

FIGS. 5 and 6 depict an exemplifying embodiment in which seal 140 can encompass first linear seal 146 and second linear seal 148, and supported element 142 can be configured at least partly as a spring element, in particular as a cup spring. First linear seal 146 can be constituted by a conical surface of sealing element 144 and a rounded surface, in particular a radius, of supported element 142. Second linear seal 148 can be formed by a rounded surface, in particular a radius, of securing element 134 and a conical surface of supported element 142. An enlargement of the respective portion A of the Figures is depicted in FIG. 5B and FIG. 6B. In a context of vibrations, for example, supported element 142 can move between first linear seal 146 and second linear seal 148 and thus ensure leak tightness. FIGS. 5B and 6B show supported element 142 in various positions between sealing element 144 and securing element 134.

What is claimed is:

1. A sensor system for sensing at least one property of a measured gas in a measured-gas space, comprising:
    a probe for sensing the property of the measured gas, the probe having at least one sensor element and at least one housing surrounding the sensor element, the housing being configured so that the sensor element in the housing is impinge-able upon by the measured gas; and
    a receiving element connectable to a wall of the measured-gas space, the probe being introducible along an insertion axis into the receiving element and securable in the receiving element;
    wherein the housing has a supported element and the receiving element has a sealing element, the supported element and the sealing element forming a seal;
    wherein with the probe introduced into the receiving element, the supported element is supported on the sealing element;
    wherein the sensor system further includes at least one securing element, the securing element being configured to secure the probe in the receiving element;
    wherein the probe seals the measured-gas space via the seal, the seal is a first linear seal, and the first linear seal prevents emergence between the probe and the receiving element of the measured gas from the measured-gas space when both: (i) the probe is in an installed state in the receiving element, and (ii) the receiving element is connected to the wall of the measured-gas space; and
    wherein the first linear seal is a conical-to-radius shaped seal.

2. The sensor system of claim 1, wherein the supported element annularly surrounds the probe.

3. The sensor system of claim 1, wherein the supported element and the sealing element are configured in a self-centering manner.

4. The sensor system of claim 1, wherein the supported element is configured at least partly as a spring element.

5. The sensor system of claim 1, wherein the seal includes at least two linear seals.

6. The sensor system of claim 1, wherein the probe is detachably connectable to the receiving element.

7. The sensor system of claim 1, wherein the at least one securing element has at least one thread having a housing-side thread and a receiving element-side thread.

8. The sensor system of claim 1, wherein the receiving element is configured as a weld-in fitting.

9. The sensor system of claim 1, wherein the supported element annularly surrounds the probe, in particular in the form of an annular shoulder.

10. The sensor system of claim 1, wherein the supported element is configured at least partly as a spring element, in particular as a cup spring.

11. The sensor system of claim 1, wherein the securing element and the supporting element form a second linear seal, the second linear seal being a conical-to-radius shaped seal, wherein the probe seals the measured-gas space via the second linear seal.

12. The sensor system of claim 1, wherein the housing includes at least one protective tube having at least one interior space and at least the sensor element received in the interior space, the protective tube being configured so that the measured gas can penetrate into the interior space.

13. The sensor system of claim 12, wherein the protective tube includes a double-walled protective tube, the double-walled protective tube having an annular gap, the measured gas being capable of flowing through the annular gap into the interior space.

14. The sensor system of claim 13, wherein the protective tube points into the measured-gas space in a tilted manner with respect to the insertion axis.

\* \* \* \* \*